(12) United States Patent
Koschmieder et al.

(10) Patent No.: US 7,690,787 B2
(45) Date of Patent: Apr. 6, 2010

(54) ARRANGEMENT FOR IMPROVING THE IMAGE FIELD IN OPHTHALMOLOGICAL APPLIANCES

(75) Inventors: Ingo Koschmieder, Jena (DE); Hans-Juergen Dobschal, Kleinromstedt (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 10/547,221

(22) PCT Filed: Dec. 20, 2003

(86) PCT No.: PCT/EP03/14689

§ 371 (c)(1),
(2), (4) Date: Aug. 24, 2005

(87) PCT Pub. No.: WO2004/073511

PCT Pub. Date: Sep. 2, 2004

(65) Prior Publication Data

US 2006/0170867 A1     Aug. 3, 2006

(30) Foreign Application Priority Data

Feb. 24, 2003   (DE)   ................. 103 07 741

(51) Int. Cl.
*A61B 3/10* (2006.01)
(52) U.S. Cl. ..................... 351/216
(58) Field of Classification Search .......... 351/216
See application file for complete search history.

(56) References Cited

U.S. PATENT DOCUMENTS 5,139,022 A   8/1992   Lempert (Continued)

FOREIGN PATENT DOCUMENTS

DE   198 12 050   9/1999

(Continued)

OTHER PUBLICATIONS

Ophthalmic optical instruments, 1987, Ferdinand Enke Verlag Stuttgart, pp. 99 ff. and 137 ff. Rassow, B., et al., "Ophthalmologisch-optische Instrumente".

*Primary Examiner*—Alicia M Harrington
(74) *Attorney, Agent, or Firm*—Eugene Ledonne; Joseph W. Treloar; Frommer Lawrence & Haug LLP

(57) ABSTRACT

The present invention is directed to an arrangement by which the image field of the illumination components and irradiation components of ophthalmic instruments for diagnosis and therapy is improved. In the arrangement according to the invention, one or more diffractive optical elements is/are arranged additionally in the illumination beam path for deliberate shaping of the image plane in the eye to be irradiated. These diffractive optical elements can be located on the surface of other optical elements, swiveled into the illumination beam path, and their wavelength changed by filters. The image plane can be adapted to the spherical contour of the eye so that the projected characters and structures have a uniformly high image quality in the center and in the edge area of the eye. The present invention is applicable for variable illumination for diagnosis and treatment of the eye, in particular for irradiation of the eye lens and other parts of the eye such as the cornea or retina. The arrangement can be used in a great variety of ophthalmic instruments such as fundus cameras, slit lamps, laser scanners, OPMI instruments or surgical microscopes.

17 Claims, 1 Drawing Sheet

U.S. PATENT DOCUMENTS

| | | | |
|---|---|---|---|
| 5,307,097 A * | 4/1994 | Baker | 351/212 |
| 5,404,884 A | 4/1995 | Lempert | |
| 5,479,221 A | 12/1995 | Heine et al. | |
| 5,571,107 A | 11/1996 | Shaibani et al. | |
| 5,673,096 A | 9/1997 | Dorsel et al. | |
| 5,980,454 A | 11/1999 | Broome | |
| 6,275,718 B1 | 8/2001 | Lempert | |
| 6,497,701 B2 | 12/2002 | Shimmick et al. | |
| 2001/0015851 A1 | 8/2001 | Danziger et al. | |
| 2002/0111606 A1 | 8/2002 | Lemberg | |

FOREIGN PATENT DOCUMENTS

| | | |
|---|---|---|
| DE | 199 43 735 | 5/2001 |
| DE | 101 21 747 | 11/2002 |
| EP | 0 331 469 | 9/1989 |
| WO | WO 00/41650 | 7/2000 |
| WO | WO 01/71411 | 9/2001 |
| WO | WO 02/45578 | 6/2002 |

* cited by examiner

ARRANGEMENT FOR IMPROVING THE IMAGE FIELD IN OPHTHALMOLOGICAL APPLIANCES

CROSS-REFERENCE TO RELATED APPLICATIONS

This application claims priority of International Application No. PCT/EP2003/014689, filed Dec. 20, 2003 and German Application No. 103 07 741.3, filed Feb. 24, 2003, the complete disclosures of which are hereby incorporated by reference.

BACKGROUND OF THE INVENTION a) Field of the Invention

The present invention is directed to an arrangement by means of which the image field of the illumination components and irradiation components of ophthalmic instruments for diagnosis and therapy is improved. The arrangement is suitable in particular for ophthalmic instruments in which it is important to achieve a uniformly high image quality over broad regions of the eye.

b) Description of the Related Art

This is the case, for example, in slit lamps. A light section is generated in the interior of the eye being examined by means of slit image projection. To ensure an exact evaluation of the section images generated in this way, a sharp imaging of the slit image is required on the visual axis as well as in the edge areas of the eye.

The present arrangement for improving the image field is usable, in principle, wherever a uniformly high image quality must be ensured over a broad area. Other applications apart from ophthalmology include, for example, laser medicine, refractive surgery and irradiation of an optical lens that is changeable by means of light according to Patents WO 00/41650 and WO 01/71411.

In this type of lens comprising a matrix of different plastics, polymerization processes are triggered by irradiation resulting in a change in the refractive index or in the shape of the lens. Intraocular lenses (IOL) of this type can be changed after implantation through directed irradiation in such a way that defective vision can be improved.

In slit lamps such as those described in [1], mechanical/optical elements such as slit diaphragms are used predominantly for generating slit images. It is difficult to achieve the variable, very small slit widths that are required for high optical detail resolution within the optical section. Further, the alignment of the mechanical subassemblies is very complicated and is made even more difficult by the thermal expansion of the subassemblies. It is almost impossible to reproduce exact slit widths. Since the slit image projection entails optical imaging with a physically limited depth of field, the image must always be focused strictly on the point of examination. A section bundle that is focused over the entire extent of the human eye cannot be achieved by the previously known solutions.

DE 198 12 050 A1 describes a method and an arrangement for the illumination in an ophthalmic microscope. A wide variety of light mark geometries is generated by means of optoelectronic components. The light field geometries are projected on the anterior and posterior portions of the eye and are used for general examination of the eye.

DE 199 43 735 A1 describes a method and an arrangement for directed irradiation of an eye by means of light from the visible and/or near infrared wavelength range. The irradiation produces irreversible chemical changes in the eye lens substance resulting in a change in the refractive index and/or in the transmission characteristics for the visible effective radiation so that it is possible to improve defective vision. For successful treatment, the distribution of the refractive power of the eye to be treated must be determined as continuously and completely as possible. The desired refractive power distribution following treatment and the data about the irradiation which is required for this are determined from these values. In this solution, it is disadvantageous that the irradiation can generally only be carried out successively point by point so that the treatment process is time-consuming. Therefore, fixation of the eyeball for the duration of treatment is indispensable.

U.S. Pat. Nos. 5,404,884; 5,139,022; and 6,275,718 describe methods and arrangements for the illumination of the anterior eye segments in which a laser with a planar configuration is used as light source. These solutions are disadvantageous in that the variability of the light field geometries is limited. Further, the system for receiving the scattered light from the eye has a physically limited depth of field which cannot fully acquire the area over which the sharp laser section image extends.

Reference:

[1] Rassow, B., et al., "Ophthalmologisch-optische Instrumente [Ophthalmic optical instruments]", 1987, Ferdinand Enke Verlag Stuttgart, pages 99 ff. and 137 ff.

In current ophthalmic instruments, the straight or even oppositely curved image planes of the illumination components and irradiation components have a disadvantageous effect. The structures projected in or on the eye have the required image sharpness at the visual axis only in the center of the image field. In the outer areas and edge areas, the fine structures fan out, become blurred and lose intensity to an appreciable extent. Accordingly, evaluation of the distortion of the structures is made harder or is only possible within a limited area.

OBJECT AND SUMMARY OF THE INVENTION

It is the primary object of the present invention to improve the image fields of the known illumination components and irradiation components of ophthalmic diagnostic instruments and therapeutic instruments in such a way that structures, images and characters projected in or on the eye have a uniformly high image quality over extensive areas of the eye.

This object is met according to the invention in an arrangement for improving the image field in ophthalmic instruments comprising an illumination beam path and one or more diffractive elements arranged additionally in the illumination beam path for deliberate shaping of the image plane.

Also, in accordance with the invention, an arrangement for improving the image field in ophthalmic instruments comprises an observation beam path and one or more diffractive optical elements arranged additionally in the observation beam path for deliberate shaping of the imaging plane.

With the present solution, a uniform image quality can be achieved over extensive areas of the eye. Accordingly, more comprehensive information can be acquired more quickly through appropriate evaluating algorithms. In particular, the solution can be applied for determining biometric data of an eye, wherein curved areas of the eye are illuminated over a large area with a very fine structure.

The invention will be described in the following with reference to an embodiment example.

DESCRIPTION OF THE PREFERRED EMBODIMENTS

Figure 1:
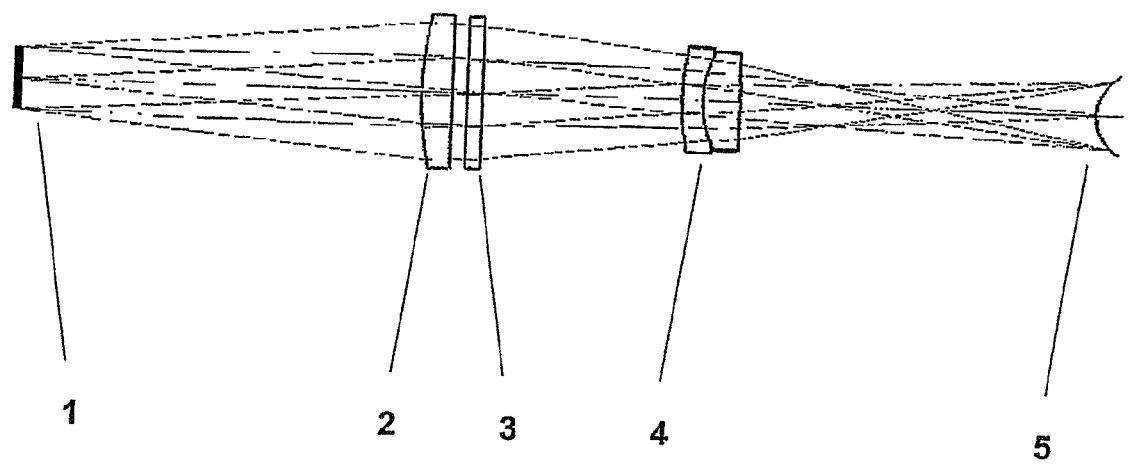
FIG. 1 is a schematic view of an illumination beam path with a diffractive optical element (DOE)
Figure 2:
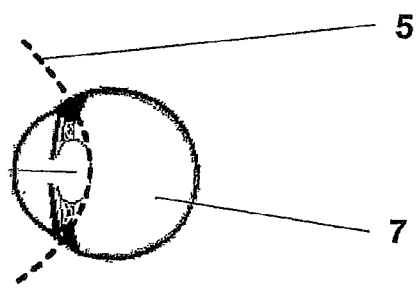
FIGS. 2 and 3 show curved image planes which are adapted to the eye.
Figure 3:
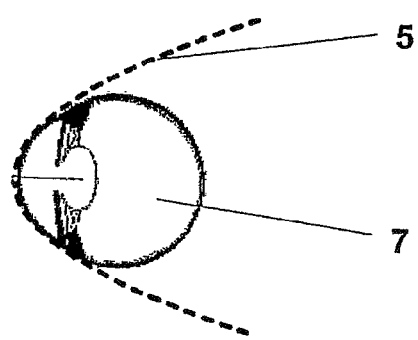

In the arrangement for improving the image field in ophthalmic instruments, a diffractive optical element (DOE) 3 is arranged in the illumination beam path of the irradiation unit in order to achieve a specific shape of the image plane 5. The diffractive optical element 3 can be located on the surface of another optical element or, as is shown in FIG. 1, can be arranged in the beam path as a separate element. The type of light source used and the type of beam shaping, i.e., structure generation or pattern generation, are not relevant (not shown). Therefore, FIG. 1 shows the beam path proceeding from the respective illumination pattern 1. Proceeding from the illumination pattern 1, the illumination beams travel to the DOE 3 through optics 2 serving as a first imaging system. The shape of the illumination beams is changed by the DOE 3 in such a way that an image plane 5 adapted to the curvature of the respective element to be irradiated results in the eye 7 to be irradiated. FIG. 2 shows an image plane 5 that is adapted to the rear surface of the eye lens; FIG. 3 shows an image plane 5 that is adapted to the front surface of the cornea.

A spherical image plane 5 that is adapted to the curvature of the eye 7 is generated by means of the arrangement, according to the invention, in the illumination beam path of ophthalmic instruments so that the projected characters or structures have a uniformly high image quality over extensive areas proceeding from the optical axis to the edge areas of the eye 7.

In another technical development, the diffractive optical element 3 is arranged in a swivelable manner. In this way, the effect can be switched on and off deliberately. The diffractive optical element 3 is optimized in connection with the total system for a defined curvature of the cornea. Consequently, for different corneal curvatures, other diffractive optical elements 3 are required which are in turn optimized in connection with the total system for this curvature of the cornea.

Since different diffractive optical elements 3 respond very sensitively with respect to wavelength, it is advantageous to combine them with appropriate color filters. In this way, the wavelength for the DOE 3 can be adapted in an optimal manner to the treatment wavelength. Accordingly, for different applications, the respective optimal DOE 3 can be used and combined with the corresponding filter. The filters and the diffractive optical elements 3 are advantageously arranged on one or more changers, e.g., slides or wheels. The diffractive optical elements 3 and the filters can be used individually or combined with one another if desired.

The arrangement for improving the image field can have, in addition, a variable, adjustable numerical aperture by which the intensity of the illumination pattern 1 in the image plane 5 can be regulated and by which the beam density in the eye 7 to be irradiated can be influenced in order to maintain the valid limiting values for the radiation dose. In the simplest case, the influence of the aperture can be exerted by means of a variable aperture diaphragm in the illumination beam path.

Further, the arrangement for improving the image field can have an adjustable focal length or back focus. Accordingly, the image position in the target area can be displaced along the optical axis in a defined manner. For example, a sharp image with a high aperture can be positioned specifically on the anterior lens surface or posterior lens surface. If needed, intermediate positions can also be freely selected. In an advantageous manner, this displacement possibility can be combined with means for monitoring distance and means for focusing. In this way, the position can also be precisely adjusted along the optical axis and maintained constant. The focusing means can be carried out based on the principle of multiple spot imaging with a high aperture so that all individual spots coincide only in the, target plane and produce an individual spot. The means for monitoring distance can be realized, for example, by means of known four-quadrant receivers which evaluate the vertex reflex of the cornea.

The function of the adjustable aperture diaphragm can advantageously be combined with the function of the adjustable back focus or focal length and the realization of dynamic patterns in order to apply specific irradiation sequences with specific patterns to certain locations without exceeding the corresponding limiting values. All of the irradiation parameters can be recorded and stored. The monitoring and correction of the position can be carried out by means of an eye-tracker unit so as to ensure an exact irradiation only in the orientated state.

The spherically curved image plane 5 which is generated by the arrangement according to the invention and is adapted to the eye 7 to be irradiated results over the observation beam path in an image plane in the eye of the observer and/or in a unit for documentation and/or archiving, which image plane is likewise compulsorily curved. By means of the additional arrangement of one or more diffractive optical elements in the observation beam path, a plane imaging plane can again be generated. This is required, for example, for photographic documentation of the implemented diagnosis and treatment and the results thereof. A uniformly high image quality can accordingly be generated over the entire plane imaging plane.

Since the diffractive optical elements react very sensitively with respect to the wavelength, it is also advantageous to combine them with corresponding color filters. The wavelength for the diffractive optical elements should be optimally adapted to an observation wavelength in order to protect the eyes of the observer from the treatment and/or diagnosis radiation.

The diffractive optical elements can be arranged on the surface of other optical elements or as separate elements in the beam path. The diffractive optical elements in the observation beam path can be swivelable like those in the illumination beam path and can be variable with respect to their wavelength by means of filters. The filters and the diffractive optical elements can be arranged on one or more changers, e.g., slides or wheels. The diffractive optical elements and the filters can be used individually or combined with one another.

The optical effects that can be achieved by using diffractive optical elements 3 in the illumination beam path can be achieved with conventional optical components such as achromats and lenses only at a substantially higher cost, if at all. The image plane can be adapted to the spherical contour of the eye so that the characters and structures projected on or in the eye have a uniformly high image quality in the center as well as in the edge area.

This is important particularly when gratings or slit structures are projected over large surfaces on the surface of the eye for measurement purposes in order to determine the biometric data through subsequent triangulation.

The present invention can also be applied for generating a variable illumination for diagnosis and treatment of the human eye, particularly for irradiation of the eye lens and other portions of the eye such as the cornea or retina. For this purpose, the arrangement for improving the image field can be used in a great variety of ophthalmic instruments such as fundus cameras, slit lamps, laser scanners, OPMI devices or surgical microscopes.

The arrangement can even be used for the irradiation of a lens inserted in the eye or for other optically active devices. In intraocular lenses made of plastic, according to WO 00/41650 and/or WO 01/71411, polymerization processes are excited by irradiation of the lens resulting in irreversible chemical changes in the lens substance. By means of these processes, the refractive index and/or the transmission behavior for the visible effective radiation or the geometric shape of the intraocular lens can be changed in a defined manner and defective vision can be improved in this way.

While the foregoing description and drawings represent the present invention, it will be obvious to those skilled in the art that various changes may be made therein without departing from the true spirit and scope of the present invention.

What invention claimed is:

1. An arrangement for improving the image field in ophthalmic instruments, comprising:
    an illumination beam path comprising illumination beams; and
    one or more diffractive optical elements being arranged additionally in the illumination beam path;
    wherein the one or more diffractive optical elements focus each of the illumination beams on the surface of the eye to deliberately shape a spherical image plane adapted to the curvature of a cornea or eye lens.

2. The arrangement for improving the image field according to claim 1, wherein the diffractive optical element or diffractive optical elements is/are located on the surface of other optical elements or arranged in the illumination beam path as separate elements.

3. The arrangement for improving the image field according to claim 1, wherein the diffractive optical element or diffractive optical elements can be swiveled into and out of the illumination beam path.

4. The arrangement for improving the image field according to claim 1, wherein the wavelength for the diffractive optical element or diffractive optical elements can be varied by means of filters.

5. The arrangement for improving the image field according to claim 1, wherein the diffractive optical elements can be swiveled into and out of the illumination beam path selectively for shaping different image planes.

6. The arrangement for improving the image field according to claim 1, wherein the different diffractive optical elements are arranged on one or more changers, wherein the diffractive optical elements can be swiveled into the illumination beam path individually or in combination with one another.

7. The arrangement for improving the image field according to claim 1, wherein different filters are arranged on one or more changers, wherein the filters can be swiveled into the illumination beam path individually or in combination with one another.

8. The arrangement for improving the image field according to claim 1, wherein the provided optical imaging system has an adjustable numerical aperture and a variable back focus.

9. The arrangement for improving the image field according to claim 1, wherein an additional unit is provided for distance monitoring and as focusing means.

10. The arrangement for improving the image field according to claim 1, wherein an eyetracker unit is provided for position monitoring and position correction.

11. An arrangement for improving the image field in ophthalmic instruments, comprising:
    an observation beam path comprising observation beams; and
    one or more diffractive optical elements being arranged additionally in the observation beam path;
    wherein the one or more diffractive optical elements focus each of the observation beams on the surface of the eye to deliberately shape a spherical image plane adapted to the curvature of a cornea or eye lens.

12. The arrangement for improving the image field according to claim 11, wherein the diffractive optical element or diffractive optical elements are located on the surface of other optical elements or are arranged in the observation beam path as separate elements.

13. The arrangement for improving the image field according to claim 11, wherein the diffractive optical element or diffractive optical elements can be swiveled into and out of the observation beam path.

14. The arrangement for improving the image field according to claim 11, wherein the wavelength for the diffractive optical element or diffractive optical elements can be varied by means of filters.

15. The arrangement for improving the image field according to claim 11, wherein the diffractive optical elements can be swiveled into and out of the observation beam path selectively for shaping different imaging planes.

16. The arrangement for improving the image field according to claim 11, wherein the different diffractive optical elements are arranged on one or more changers, wherein the diffractive optical elements can be swiveled into the observation beam path individually or in combination with one another.

17. The arrangement for improving the image field according to claim 11, wherein different filters are arranged on one or more changers, wherein the filters can be swiveled into the observation beam path individually or in combination with one another.

* * * * *